United States Patent [19]

Li

[11] Patent Number: 5,264,044

[45] Date of Patent: * Nov. 23, 1993

[54] METHOD OF CLEANING USING HYDROCHLOROFLUOROCARBONS HAVING A TERTIARY STRUCTURE

[75] Inventor: Chien C. Li, East Aurora, N.Y.

[73] Assignee: AlliedSignal Inc., Morristown, N.J.

[*] Notice: The portion of the term of this patent subsequent to Oct. 27, 2009 has been disclaimed.

[21] Appl. No.: 878,135

[22] Filed: May 4, 1992

Related U.S. Application Data

[62] Division of Ser. No. 767,004, Sep. 27, 1991, Pat. No. 5,146,015.

[51] Int. Cl.$^5$ .......................... B08B 3/08; C11D 7/50; C23G 5/028
[52] U.S. Cl. ........................................ 134/40; 134/42; 252/162; 252/172; 252/364
[58] Field of Search ............................ 134/40, 38, 42; 252/162, 171, 172, 364

[56] References Cited

U.S. PATENT DOCUMENTS

| | | |
|---|---|---|
| 2,716,141 | 8/1955 | Miller . |
| 3,046,304 | 7/1962 | Haszeldine . |
| 3,317,618 | 5/1967 | Haszeldine . |
| 4,947,881 | 8/1990 | Magid et al. .......................... 134/40 |
| 4,954,289 | 9/1990 | Bartlett et al. ..................... 134/40 X |
| 4,986,928 | 1/1991 | Merchant .......................... 134/40 X |
| 5,034,149 | 7/1991 | Merchant . |
| 5,064,559 | 11/1991 | Merchant et al. .................. 252/171 |
| 5,122,294 | 6/1992 | Logsdon et al. .................... 252/171 |
| 5,146,015 | 9/1992 | Li ....................................... 570/134 |
| 5,152,845 | 10/1992 | Li ......................................... 134/40 |
| 5,158,617 | 10/1992 | Li ......................................... 134/40 |

FOREIGN PATENT DOCUMENTS 0347924 12/1989 European Pat. Off. .
WO90/08814 8/1990 Int'l Pat. Institute .

OTHER PUBLICATIONS

Atkinson, "Kinetics and Mechanism of the Gas-Phase Reaction of the Hydroxy Radical with Organic Compounds", Chem. Rev. 86, 69 (1986).

Taylor et al., "Laser Photolysis/Laser-Induced Fluorescence Studies of Reaction Rates of OH with $CH_3Cl$, $CH_2Cl_2$, and $CHCl_3$ over an Extended Temperature Range", Int. J. of Chem. Kinetics 21, 829 (1989).

Primary Examiner—Theodore Morris
Assistant Examiner—Saeed T. Chaudhry
Attorney, Agent, or Firm—Melanie L. Brown; Darryl L. Webester; Jay P. Friedenson

[57] ABSTRACT

The present invention provides a class of hydrochlorofluorocarbons having a tertiary structure, 5 carbon atoms, 1 chlorine atom, 6 to 8 fluorine atoms, and OH rate constants from about 8 to about 15 $cm^3$/molecule-sec$\times 10^{-14}$. The hydrochlorofluorocarbons are useful as solvents and blowing agents.

16 Claims, No Drawings

METHOD OF CLEANING USING HYDROCHLOROFLUOROCARBONS HAVING A TERTIARY STRUCTURE

This application is a division of application Ser. No. 767,004, filed Sep. 27, 1991, now U.S. Pat. No. 5,146,015.

BACKGROUND OF THE INVENTION

The present invention relates to a class of hydrochlorofluorocarbons which have tertiary structures, 5 carbon atoms, 1 chlorine atom, 6 to 8 fluorine atoms, and OH rate constants from about 8 to about 15 $cm^3/molecule/sec \times 10^{-14}$.

Vapor degreasing and solvent cleaning with fluorocarbon based solvents have found widespread use in industry for the degreasing and otherwise cleaning of solid surfaces, especially intricate parts and difficult to remove soils.

In its simplest form, vapor degreasing or solvent cleaning consists of exposing a room-temperature object to be cleaned to the vapors of a boiling solvent. Vapors condensing on the object provide clean distilled solvent to wash away grease or other contamination. Final evaporation of solvent from the object leaves behind no residue as would be the case where the object is simply washed in liquid solvent.

For soils which are difficult to remove, where elevated temperature is necessary to improve the cleaning action of the solvent, or for large volume assembly line operations where the cleaning of metal parts and assemblies must be done efficiently and quickly, the conventional operation of a vapor degreaser consists of immersing the part to be cleaned in a sump of boiling solvent which removes the bulk of the soil, thereafter immersing the part in a sump containing freshly distilled solvent near room temperature, and finally exposing the part to solvent vapors over the boiling sump which condense on the cleaned part. In addition, the part can also be sprayed with distilled solvent before final rinsing.

Vapor degreasers suitable in the above-described operations are well known in the art. For example, Sherliker et al. in U.S. Pat. No. 3,085,918 disclose such suitable vapor degreasers comprising a boiling sump, a clean sump, a water separator, and other ancilliary equipment.

Cold cleaning is another application where a number of solvents are used. In most cold cleaning applications, the soiled part is either immersed in the fluid or wiped with rags or similar objects soaked in solvents.

In cold cleaning applications, the use of the aerosol packaging concept has long been found to be a convenient and cost effective means of dispensing solvents. Aerosol products utilize a propellant gas or mixture of propellant gases, preferably in a liquefied gas rather than a compressed gas state, to generate sufficient pressure to expel the active ingredients, i.e. product concentrates such as solvents, from the container upon opening of the aerosol valve. The propellants may be in direct contact with the solvent, as in most conventional aerosol systems, or may be isolated from the solvent, as in barrier-type aerosol systems.

Chlorofluorocarbon solvents, such as trichlorotrifluoroethane, have attained widespread use in recent years as effective, nontoxic, and nonflammable agents useful in degreasing applications and other solvent cleaning applications. Trichlorotrifluoroethane has been found to have satisfactory solvent power for greases, oils, waxes and the like. It has therefore found widespread use for cleaning electric motors, compressors, heavy metal parts, delicate precision metal parts, printed circuit boards, gyroscopes, guidance systems, aerospace and missile hardware, aluminum parts and the like. Trichlorotrifluoroethane has two isomers: 1,1,2-trichloro-1,2,2-trifluoroethane (known in the art as CFC-113) and 1,1,1-trichloro-2,2,2-trifluoroethane (known in the art as CFC-113a). CFC-113 has a boiling point of about 470° C. and has been found to have satisfactory solvent power for greases, oils, waxes, and the like.

Another commonly used solvent is chloroform (known in the art as HCC-20) which has a boiling point of about 63° C. Perchloroethylene is a commonly used dry cleaning and vapor degreasing solvent which has a boiling point of about 121° C. These compounds are disadvantageous for use as solvents because they are toxic; also, chloroform causes liver damage when inhaled in excess.

Although chlorine is known to contribute to the solvency capability of a compound, fully halogenated chlorofluorocarbons and hydrochlorofluorocarbons are suspected of causing environmental problems in connection with the earth's protective ozone layer. Thus, the art is seeking new compounds which do not contribute to environmental problems but yet provide the solvency properties of CFC-113.

Chlorofluorocarbons (CFCS) such as CFC-113 are suspected of causing environmental problems in connection with the ozone layer. Under the Clean Air Act, CFC-113 is being phased-out of production.

In response to the need for stratospherically safe materials, substitutes have been developed and continue to be developed. *Research Disclosure* 14623 (Jun. 1978) reports that 1,1-dichloro-2,2,2-trifluoroethane (known in the art as HCFC-123) is a useful solvent for degreasing and defluxing substrates. In the EPA "Findings of the Chlorofluorocarbon Chemical Substitutes International Committee", EPA-600/9-88-009 (Apr. 1988), it was reported that HCFC-123 and 1,1-dichloro-1-fluoroethane (known in the art as HCFC-141b) have potential as replacements for CFC-113 as cleaning agents.

The problem with these substitutes is that they have a long atmospheric lifetime as determined by their reaction with OH radicals in the troposphere. Table I below contains the OH rate constants and corresponding atmospheric lifetimes for these substitutes. In Table I, Exp $K_{OH}$ stands for experimental $K_{OH}$ rate constant, Est $K_{OH}$ stands for estimated $K_{OH}$ rate constant, Exp Life stands for experimental lifetime, and Est Life stands for estimated lifetime. The unit on the rate constant is $cm^3/molecule/sec \times 10^{-14}$ and the unit on the lifetime is years.

TABLE I

| Number | Formula | Exp $K_{OH}$ | Est $K_{OH}$ | Exp Life | Est Life |
|---|---|---|---|---|---|
| HCFC-123 | $CHCl_2CF_3$ | 3.7 | 2.96 | 2.0 | 2.6 |
| HCFC-124 | $CF_3CHClF$ | 1.0 | 1.00 | 7.5 | 7.5 |
| HCFC-141b | $CFCl_2CH_3$ | 0.75 | 2.10 | 10.1 | 3.6 |
| HCFC-142b | $CF_2ClCH_3$ | 0.38 | 2.10 | 19.9 | 6 |
| HCFC-225ca | $CF_3CF_2CHCl_2$ | 2.49 | 3.30 | 2.3 | 2.3 |
| HCFC-225cb | $CClF_2CF_2CHClF$ | 0.91 | 3.86 | 2 | 1.96 |
| HCC-140 | $CCl_3CH_3$ | 1.2 | 1.21 | 6.3 | 6.3 |

It would be desirable to have substitutes with OH rate constants of at least about 8 cm$^3$/Molecule/sec$\times 10^{-14}$ which equates to an atmospheric lifetime of 12 months or less.

If the OH rate constant of a compound is too high, the compound is a VOC (Volatile Organic Compound) because it is so reactive that it forms carbon dioxide which contributes to global warming. Thus, it would be desirable to have substitutes with OH rate constants of 15 cm$^3$/molecule/sec$\times 10^{-14}$ or less which equates to an atmospheric lifetime of at least 6 months.

Commonly assigned U.S. Pat. No. 4,947,881 teaches a method of cleaning using hydrochlorofluoropropanes having 2 chlorine atoms and a difluoromethylene group. European Publication 347,924 published Dec. 27, 1989 teaches hydrochlorofluoropropanes having a difluoromethylene group. International Publication Number WO 90/08814 published Aug. 9, 1990 teaches azeotropes having at least one hydrochlorofluoropropane having a difluoromethylene group.

A wide variety of consumer parts is produced on an annual basis in the United States and abroad. Many of these parts have to be cleaned during various manufacturing stages in order to remove undesirable contaminants. These parts are produced in large quantities and as a result, substantial quantities of solvents are used to clean them.

Thus, hydrochlorofluorocarbons having OH rate constants between about 8 and about 15 cm$^3$/molecule/sec$\times 10^{-14}$ and which are useful in many applications including as solvents are needed in the art.

SUMMARY OF THE INVENTION

Hydrochlorofluorocarbons having tertiary structures, 5 carbon atoms, 1 chlorine atom, and 6 to 8 fluorine atoms total over 337 compounds. Out of this over 337 compounds, I was surprised to find a class of 14 hydrochlorofluorocarbons having OH rate constants from about 8 to about 15 cm$^3$/molecule/sec$\times 10^{-14}$. The 14 hydrochlorofluorocarbons have tertiary or quaternary structures. The term "tertiary" as used herein means that at least one carbon atom is directly bonded to three carbon atoms.

The OH rate constant can be determined by any method known in the art. For example, see Atkinson, "Kinetics and Mechanisms of the Gas-Phase Reactions of the Hydroxyl Radical with Organic Compounds under Atmospheric Conditions", Chem. Rev. 86, 69 (1986) and Taylor et al., "Laser Photolysis/Laser-Induced Fluorescence Studies of Reaction Rates of OH with CH$_3$Cl, CH$_2$Cl$_2$, and CHCl$_3$ over an Extended Temperature Range", Int. J. of Chem. Kinetics 21, 829 (1989).

The hydrochlorofluorocarbons having a tertiary structure are listed in Table II below. The unit on the calculated K$_{OH}$ is cm$^3$/Molecule/sec$\times 10^{-14}$ and the unit on the calculated lifetime is months in Table II.

TABLE II

| CHEMICAL FORMULA | K$_{OH}$ | LIFETIME |
|---|---|---|
| CF$_3$C(CF$_3$)(H)CFClCH$_3$ | 9.0 | 10 |
| CF$_2$ClC(CF$_3$)(H)CF$_2$CH$_3$ | 11.3 | 8 |
| CF$_2$HC(CH$_3$)(Cl)CF$_2$CF$_3$ | 13.0 | 7 |
| CF$_3$C(CH$_3$)(Cl)CFHCF$_3$ | 13.0 | 7 |
| CF$_2$HC(CH$_3$)(F)CF$_2$CF$_2$Cl | 15.1 | 6 |
| CFClHC(CH$_3$)(F)CF$_2$CF$_3$ | 15.1 | 6 |
| CF$_2$HC(CH$_3$)(F)CFClCF$_3$ | 15.1 | 6 |
| CF$_3$C(CH$_3$)(F)CFHCF$_2$Cl | 15.1 | 6 |
| CF$_2$ClC(CH$_3$)(F)CFHCF$_3$ | 15.1 | 6 |

TABLE II-continued

| CHEMICAL FORMULA | K$_{OH}$ | LIFETIME |
|---|---|---|
| CF$_2$ClC(CF$_2$H)(F)CF$_2$CH$_3$ | 15.1 | 6 |
| CF$_3$(CF$_3$)(Cl)CH$_2$CFH$_2$ | 11.3 | 8 |
| CF$_3$C(CF$_2$Cl)(F)CH$_2$CF$_2$H | 13.0 | 7 |
| CF$_3$C(CF$_3$)(H)CHClCH$_3$ | 13.0 | 7 |
| CF$_3$C(CF$_3$)(F)CH$_2$CClH$_2$ | 8.2 | 11 |

This present class with its OH rate constants between about 8 to about 15 cm$^3$/molecule/sec$\times 10^{-14}$ was unexpected. I discovered this when I compared isomers having the chlorine atom in the same position as the covered compound. This is shown in the Comparatives below.

The present hydrofluorocarbons may be used in any applications including as solvents.

Other advantages of the present invention will become apparent from the following description.

DESCRIPTION OF THE PREFERRED EMBODIMENTS

Known methods for making hydrochlorofluorocarbons can be modified in order to form the tertiary hydrochlorofluorocarbons having 5 carbon atoms, 1 chlorine atom, and 6 to 8 fluorine atoms of the present invention.

As an example, 2-methyl-2-difluoromethyl-1-chloro-1,1,3,3,3-trifluoropropane may be prepared as follows. Commercially available 1,1-dichloropropene may be reacted with commercially available trifluoromethyl iodide to form 1,1-dichloro-1-iodo-2-trifluoromethylpropane which may be dehydrohalogenated to form 1,1-dichloro-2-trifluoromethyl-1-propene. The 1,1-dichloro-2-trifluoromethyl-1-propene may be hydrogenated to form 1,1-dichloro-2-trifluoromethylpropane which may be fluorinated to form 1,1-difluoro-2-trifluoromethylpropane. The 1,1-difluoro-2-trifluoromethylpropane may be dehydrogenated to form 1,1-difluoro-2-trifluoromethyl-1-propene which may be reacted with commercially available trifluoromethyl iodide to form 1,1-difluoro-1-iodo-2,2-trifluoromethylpropane. The 1,1-difluoro-i-iodo-2,2-trifluoromethylpropane may be chlorinated to form 1-chloro-1,1-difluoro-2, 2-trifluoromethylpropane which may be hydrogenated to form 2-methyl-2-difluoromethyl-1-chloro-1,1,3,3,3-trifluoropropane.

As another example, 2-trifluoromethyl-3-chloro-1,1,1,3-tetrafluorobutane may be prepared by fluorinating commercially available 2-butanone and then chlorinating to form 2-chloro-2-fluorobutane which may then be dehydrogenated to form 3-chloro-3-fluoro-1-butene. CF$_3$ may then be added to the 3-chloro-3-fluoro-1-butene to form 2-trifluoromethyl-3-chloro-1,3-difluorobutane which may then be dehydrogenated to form 2-trifluoromethyl-3-chloro-1,3-difluoro-1-butene. The 2-trifluoromethyl-3-chloro-1,3-difluoro-1-butene may then be reacted with hydrogen fluoride to form 2-difluoromethyl-3-chloro-1,1,1,3-tetrafluorobutane which may then be dehydrogenated to form 2-trifluoromethyl-3-chloro-1,1,1,3-tetrafluoro-1-butene which may then be reacted with hydrogen fluoride to form 2-trifluoromethyl-3-chloro-1,1,1,3-tetrafluorobutane.

As another example, 2-trifluoromethyl-1-chloro-1,1,3,3-tetrafluorobutane may be prepared by fluorinating commercially available 2-butanone to form 2,2-difluorobutane which may then be dehydrogenated to form 3,3-difluoro-1-butene. CF$_3$ may then be added to the 3,3-difluoro-1-butene to form 2-trifluoromethyl-1,3,3-trifluorobutane which may then be dehydrogenated to form 2-trifluoromethyl-1,3,3-trifluoro-1-butene. The 2-trifluoromethyl-1,3,3-trifluoro-1-butene may then be reacted with hydrogen fluoride to form 2-difluoromethyl-1,1,1,3,3-pentafluorobutane which may then be dehydrogenated to form 2-trifluoromethyl-1,1,3,3-tetrafluoro-1-butene which may then be reacted with hydrogen chloride to form 2-trifluoromethyl-1-chloro-1,1,3,3-tetrafluorobutane.

As another example, 2-chloro-2-methyl-1,1,3,3,4,4-heptafluorobutane may be prepared by fluorinating commercially available 2-methyl-butene-3-yne to form 2-methyl-1,2,3,3,4,4-hexafluorobutane which may then be dehalohydrogenated to form 2-methyl-1,3,4,4-tetrafluoro-1,3-butadiene. The 2-methyl-1,3,4,4-tetrafluoro-1,3-butadiene may then be fluorinated to form 2-methyl-1,1,3,3,4,4-hexafluorobutane which may then be dehalohydrogenated to form 2-methyl-1,1,3,3,4,4,4-hexafluoro-1-butene. The 2-methyl-1,1,3,3,4,4-hexafluoro-1-butene may then be reacted with hydrogen chloride to form 2-chloro-2-methyl-1,1,3,3,4,4,4-heptafluorobutane.

As another example, 2-chloro-2-methyl-1,1,1,3,4,4,4-hexafluorobutane may be prepared by fluorinating commercially available 2-methyl-1-buten-3-yne to form 2-methyl-1,2,3,3,4,4,4-heptafluorobutane which may then be dehydrohalogenated to form 2-methyl-1,3,4,4-tetrafluoro-1,3-butadiene. The 2-methyl1,3,4,4-tetrafluoro-1,3-butadiene may then be fluorinated to form 2-methyl-1,1,2,3,3,4,4,4-octafluorobutane which may then be dehalogenated to form 2-methyl-1,1,3,4,4,4-hexafluoro-2-butene. The 2-methyl-1,1,3,4,4,4-hexafluoro-2-butene may then be hydrogenated to form 2-methyl-1,1,3,4,4,4-hexafluorobutane which may then be dehydrogenated to form 2-methyl-1,1,3,4,4,4-hexafluoro-1-butene. The 2-methyl-1,1,3,4,4,4-hexafluoro-1-butene may then be chlorofluorinated to form 2-chloro-2-methyl-1,1,1,3,4,4,4-hexafluorobutane.

As another example, 2-methyl-4-chloro-1,1,2,3,3,4,4-heptafluorobutane may be prepared by fluorinating commercially available 2-methyl-1-buten-3-yne to form 2-methyl-1,2,3,3,4,4-hexafluorobutane which may then be dehydrohalogenated to form 2-methyl-1,3,4,4-tetrafluoro-1,3-butadiene. The 2-methyl-1,3,4,4-tetrafluoro-1,3-butadiene may then be chlorofluorinated to form 2-methyl-4-chloro-1,1,2,3,3,4,4-heptafluorobutane.

As another example, 2-methyl-1-chloro-1,2,3,3,4,4,4-heptafluorobutane may be prepared by fluorinating commercially available 2-methyl-1-buten-3-yne to form 2-methyl-1,2,3,3,4,4-hexafluorobutane which may then be dehydrohalogenated to form 2-methyl-1,3,4,4-tetrafluoro-1,3-butadiene. The 2-methyl-1,3,4,4-tetrafluoro-1,3-butadiene may then be fluorinated to form 2-methyl-1,1,2,3,3,4,4,4-octafluorobutane which may then be dehalogenated to form 2-methyl-1,3,3,4,4,4-hexafluoro-1-butene. The 2-methyl-1,3,3,4,4,4-hexafluoro-1-butene may then be chlorofluorinated to form 2-methyl-1-chloro-1,2,3,3,4,4,4-heptafluorobutane.

As another example, 2-methyl-3-chloro-1,1,2,3,4,4,4-heptafluorobutane may be prepared by fluorinating commercially available 2-methyl-1-buten-3-yne to form 2-methyl-1,2,3,3,4,4-hexafluorobutane which may then be dehydrohalogenated to form 2-methyl-1,3,4,4-tetrafluoro-1,3-butadiene. The 2-methyl-1,3,4,4-tetrafluoro-1,3-butadiene may then be fluorinated to form 2-methyl-1,1,2,3,3,4,4,4-octafluorobutane which may then be dehalogenated to form 2-methyl-1,1,3,4,4,4-hexafluoro-2-butene. The 2-methyl-1,1,3,4,4,4-hexafluoro-2-butene may then be chlorofluorinated to form 2-methyl-3-chloro-1,1,2,3,4,4,4-heptafluorobutane.

As another example, 2-methyl-4-chloro-1,1,1,2,3,4,4-heptafluorobutane may be prepared by fluorinating 2-methyl-1-bute-3-yne to form 2-methyl-1,2,3,3,4,4-hexafluorobutane which may then be dehydrohalogenated to form 2-methyl-1,3,4,4-tetrafluoro-1,3-butadiene. The 2-methyl-1,3,4,4-tetrafluoro-1,3-butadiene may then be chlorofluorinated to form 2-methyl-4-chloro-1,1,2,3,3,4,4-heptafluorobutane which may then be dehalogenated to form 2-methyl-4-chloro-1,1,3,4,4-pentafluoro-2-butene. The 2-methyl-4-chloro-1,1,3,4,4-pentafluoro-2-butene may then be hydrogenated to form 2-methyl-4-chloro-1,1,3,4,4-pentafluorobutane which may then be hydrogenated to form 2-methyl-4-chloro-1,2,3,4,4-pentafluoro-1-butene. The 2-methyl-4-chloro-1,1,3,4,4-pentafluoro-1-butene may then be fluorinated to form 2-methyl-4-chloro-1,1,1,2,3,4,4-heptafluorobutane.

As another example, 2-trifluoromethyl-1-chloro-1,1,3,3-tetrafluorobutane may be prepared by fluorinating commercially available 2-butanone to form 2,2-difluorobutane which may then be dehydrogenated to form 3,3-difluoro-1-butene. CF$_3$ may then be added to the 3,3-difluoro-1-butene to form 2-trifluoromethyl-1,3,3-trifluorobutane which may then be dehydrogenated to form 2-trifluoromethyl-1,2,3-trifluoro-1-butene. The 2-trifluoromethyl-1,3,3-trifluoro-1-butene may then be fluorinated to form 2-trifluoromethyl-1,1,2,3,3-pentafluorobutane which may then be dehydrohalogenated to form 2-trifluoromethyl-1,1,3,3-tetrafluoro-1-butene. The 2-trifluoromethyl-1,1,3,3-tetrafluoro-1-butene may then be reacted with hydrogen chloride to form 2-trifluoromethyl-1-chloro-1,1,3,3-tetrafluorobutane.

As another example, 2-methyl-1-chloro-1,1,2,3,4,4,4-heptafluorobutane may be prepared by fluorinating commercially available 2-methyl-1-bute-3-yne to form 2-methyl-1,1,3,3,4,4-hexafluorobutane which may then be dehydrohalogenated to form 2-methyl-1,3,4,4-tetrafluoro-1,3-butadiene. The 2-methyl-1,3,4,4-tetrafluoro-1,3-butadiene may then be fluorinated to form 2-methyl-1,1,2,3,3,4,4,4-octafluorobutane which may then be dehalogenated to form 2-methyl-1,1,3,4,4,4-hexafluoro-2-butene. The 2-methyl-1,1,3,4,4,4-hexafluoro-2-butene may then be hydrogenated to form 2-methyl-1,1,3,4,4,4-hexafluorobutane which may then be dehydrogenated to form 2-methyl-1,1,3,4,4,4-hexafluoro-1-butene. The 2-methyl-1,1,3,4,4,4-hexafluoro-1-butene may then be chlorofluorinated to form 2-methyl-1-chloro-1,1,2,3,4,4,4-heptafluorobutane.

As another example, 2-difluoromethyl-1-chloro-1,1,2,3,3-pentafluorobutane may be prepared by fluorinating commercially available 2-butanone to form 2,2-difluorobutane which may then be dehydrogenated to form 3,3-difluoro-1-butene. CF$_3$ may then be added to the 3,3-difluoro-1-butene to form 2-trifluoromethyl-1,3,3-trifluorobutane which may then be dehydrogenated to form 2-trifluoromethyl-1,3,3-trifluoro-1-butene. The 2-trifluoromethyl-1,3,3-trifluoro-1-butene may then be fluorinated to form 2-trifluoromethyl-1,1,2,3,3-pentafluorobutane which may then be dehalogenated to form 2-difluoromethyl-1,1,3,3-tetrafluoro-1-butene. The 2-difluoromethyl-1,1,3,3-tetrafluoro-1-butene may then be chlorofluorinated to form 2-difluoromethyl-1-chloro-1,1,2,3,3-pentafluorobutane.

As another example, 2-chloro-2-trifluoromethyl-1,1,1,4-tetrafluorobutane may be prepared by reacting vinyl fluoride according to the procedure of George L. Fleming et al., "Addition of Free Radicals to Unsaturated Systems. Part XX. The Direction of Radical Addition of Heptafluoro-2-iodopropane to Vinyl Fluoride, Trifluoroethylene, and Hexafluoropropene", J. C. S. Perkin I, 574 (1973) to form a product which may then be reacted with hydrogen chloride to form 2-chloro-2-trifluoromethyl-1,1,1,4-tetrafluorobutane.

As another example, 2-trifluoromethyl-1-chloro-1,1,2,4,4-pentafluorobutane may be prepared by reacting commercially available 1,1-difluoroethylene according to the procedure of George L. Fleming et al., supra, to form a product which may then be hydrogenated to form 2-trifluoromethyl-1,1,1,2,4,4-hexafluorobutane which may then be chlorinated to form 2-trifluoromethyl-1-chloro-1,1,2,4,4-pentafluorobutane.

An another example, 2-trifluoromethyl-3-chloro-1,1,1-trifluorobutane may be prepared by reacting commercially available ethylene according to the procedure of George L. Fleming et al., to form a product which may then be reacted with hydrogen chloride to form 2-trifluoromethyl-3-chloro-1,1,1-trifluorobutane.

As another example, 2-trifluoromethyl-4-chloro-1,1,1,2-tetrafluorobutane may be prepared by reacting vinyl chloride according to the procedure of George L. Fleming et al., supra, to form a product which may then be reacted with hydrogen fluoride to form 2-trifluoromethyl-4-chloro-1,1,1,2-tetrafluorobutane.

The preferred hydrochlorofluorocarbons of the present invention are $CF_3C(CF_3)(H)CFClCH_3$; $CF_2ClC(CF_3)(H)CF_2CH_3$; $CF_2HC(CH_3)(Cl)CF_2CF_3$; $CF_3C(CH_3)(Cl)CFHCF_3$; $CF_3C(CF_3)(H)CClHCH_3$; and $CF_3C(CF_3)(F)CH_2CH_2Cl$.

The present hydrochlorofluorocarbons may be used as solvents in vapor degreasing, solvent cleaning, cold cleaning, dewatering, dry cleaning, defluxing, decontamination, spot cleaning, aerosol propelled rework, extraction, particle removal, and surfactant cleaning applications. In these uses, the object to be cleaned is immersed in one or more stages in the liquid and/or vaporized solvent or is sprayed with the liquid solvent. Elevated temperatures, ultrasonic energy, and/or agitation may be used to intensify the cleaning effect.

The present hydrochlorofluorocarbons are also useful as blowing agents, Rankine cycle and absorption refrigerants, and power fluids and especially as refrigerants for centrifugal refrigeration chillers.

The present invention is more fully illustrated by the following non-limiting Examples.

COMPARATIVES

COMP stands for Comparative in the following Tables III through VII.

$CF_3C(CF_3)(H)CFClCH_3$ and $CF_2HC(CH_3)(F)CFClCF_3$ of the present invention have $K_{OH}$ values of 9.0 and 15.1 m$^3$/molecule/secx$10^{-14}$ respectively as shown in Table II above. In contrast, the isomers having the chlorine atom in the same position shown in Comparatives A through E in Table III below have $K_{OH}$ values outside of the range of the present compounds. The unit on the $K_{OH}$ is cm$^3$/molecule/secx$10^{-14}$ and the unit on the lifetime is months in Table III below.

TABLE III

| COMP | CHEMICAL FORMULA | $K_{OH}$ | LIFETIME |
|---|---|---|---|
| A | $CF_3C(CH_3)(H)CFClCF_3$ | 6.9 | 13.1 |
| B | $CF_2HC(CF_2H)(H)CFClCF_2H$ | 20.8 | 4.4 |
| C | $CFH_2C(CF_2H)(F)CFClCF_2H$ | 22.5 | 4.0 |
| D | $CFH_2C(CF_3)(F)CFClCFH_2$ | 20.4 | 4.5 |
| E | $CF_2HC(CF_3)(H)CFClCFH_2$ | 19.7 | 4.6 |

$CF_2ClC(CF_3)(H)CF_2CH_3$; $CF_2ClC(CH_3)(F)CFHCF_3$; $CF_2ClC(CF_2H)(F)CF_2CH_3$; and $CF_3C(CF_2Cl)(F)CH_2CF_2H$ of the present invention have $K_{OH}$ values of 11.3, 15.1, 15.5, and 13.0 cm$^3$/molecule/secx$10^{-14}$ respectively as shown in Table II above. In contrast, the isomers having the chlorine atom in the same position shown in comparatives F through N in Table IV below have $K_{OH}$ values greater than 15 cm$^3$/molecule/secx$10^{-14}$. The unit on the $K_{OH}$ is cm$^3$/molecule/secx$10^{-14}$ and the unit on the lifetime is months in Table IV below.

TABLE IV

| COMP | CHEMICAL FORMULA | $K_{OH}$ | LIFETIME |
|---|---|---|---|
| F | $CF_2ClC(CF_2H)(F)CH_2CF_2H$ | 19.0 | 4.8 |
| G | $CF_2ClC(CF_2H)(F)CFHCFH_2$ | 20.2 | 4.5 |
| H | $CF_2ClC(H)(CF_2H)CF_2CFH_2$ | 19.9 | 4.6 |
| I | $CF_2ClC(H)(CF_3)CH_2CF_2H$ | 15.4 | 5.9 |
| J | $CF_2ClC(H)(CF_3)CFHCFH_2$ | 17.0 | 5.3 |
| K | $CF_2ClC(H)(CF_2H)CH_2CF_3$ | 16.5 | 5.5 |
| L | $CF_2ClC(H)(CF_2H)CFHCF_2H$ | 19.6 | 4.6 |
| M | $CF_2ClC(F)(CFH_2)CH_2CF_3$ | 17.7 | 5.1 |
| N | $CF_2ClC(F)(CFH_2)CFHCF_2H$ | 21.0 | 4.3 |

$CF_2HC(CH_3)(Cl)CF_2CF_3$; $CF_3C(CH_3)(Cl)CFHCF_3$; and $CF_3C(CF_3)(Cl)CH_2CFH_2$ of the present invention have $K_{OH}$ values of 13.0, 13.0, and 11.3 cm$^3$/molecule/secx$10^{-14}$ respectively as shown in Table II above. In contrast, the isomers having the chlorine atom in the same position shown in Comparatives O through U in Table V below have $K_{OH}$ values outside of the range of the present compounds. The unit on the $K_{OH}$ is cm$^3$/molecule/secx$10^{-14}$ and the unit on the lifetime is months in Table V below.

TABLE V

| COMP | CHEMICAL FORMULA | $K_{OH}$ | LIFETIME |
|---|---|---|---|
| O | $CF_3C(CF_3)(Cl)CFHCH_3$ | 5.2 | 17.4 |
| P | $CF_2HC(CF_2H)(Cl)CF_2CFH_2$ | 22.5 | 4.0 |
| Q | $CF_2HC(CF_3)(Cl)CH_2CF_2H$ | 18.6 | 4.9 |
| R | $CF_3C(CF_2H)(Cl)CFHCFH_2$ | 20.0 | 4.5 |
| S | $CF_2HC(CF_2H)(Cl)CH_2CF_3$ | 19.7 | 4.6 |
| T | $CF_2HC(Cl)(CF_3)CF_2CH_3$ | 15.7 | 5.8 |
| U | $CF_2HC(CF_2H)(Cl)CFHCF_2H$ | 22.0 | 4.1 |

$CF_2HC(CH_3)(F)CF_2CF_2Cl$, $CF_3C(CH_3)(F)CFHCF_2Cl$; and $CF_3C(CF_3)(F)CH_2CClH_2$ of the present invention have $K_{OH}$ values of 15.1, 15.1, and 8.2 cm$^3$/molecule/secx$10^{-14}$ respectively as shown in Table II above. In contrast, the isomers having the chlorine atom in the same position shown in Comparatives W through BB in Table VI below have $K_{OH}$ values greater than 15 cm$^3$/molecule/secx$10^{-14}$. The unit on the $K_{OH}$ is cm$^3$/molecule/secx$10^{-14}$ and the unit on the lifetime is months in Table VI below.

TABLE VI

| COMP | CHEMICAL FORMULA | $K_{OH}$ | LIFETIME |
|---|---|---|---|
| W | $CF_2HC(F)(CF_2H)CH_2CF_2Cl$ | 19.9 | 4.6 |

TABLE VI-continued

| COMP | CHEMICAL FORMULA | $K_{OH}$ | LIFETIME |
|---|---|---|---|
| X | $CF_2HC(F)(CF_2H)CFHCFHCl$ | 20.7 | 4.4 |
| Y | $CF_2HC(F)(CF_2H)CF_2CH_2Cl$ | 18.8 | 4.8 |
| Z | $CF_2HC(F)(CF_3)CH_2CFHCl$ | 17.3 | 5.2 |
| AA | $CF_2HC(F)(CF_3)CFHCH_2Cl$ | 16.4 | 5.5 |
| BB | $CF_2HC(H)(CF_3)CFHCFHCl$ | 18.2 | 5.0 |

$CF_3C(CF_3)(H)CHClCH_3$ of the present invention has a $K_{OH}$ value of 13 cm$^3$/molecule/sec×10$^{-14}$ as shown in Table II above. In contrast, the isomers having the chlorine atom in the same position shown in Comparatives CC through HH in Table VII below have $K_{OH}$ values greater than 15 cm$^3$/molecule/sec×10$^{-14}$. The unit on the $K_{OH}$ is cm$^3$/molecule/sec×10$^{-14}$ and the unit on the lifetime is months in Table VII below.

TABLE VII

| COMP | CHEMICAL FORMULA | $K_{OH}$ | LIFETIME |
|---|---|---|---|
| CC | $CFH_2C(CF_2H)(F)CClHCFH_2$ | 27.8 | 3.3 |
| DD | $CF_2HC(CF_2H)(F)CFClCH_3$ | 30.8 | 2.9 |
| EE | $CF_3C(CF_2H)(F)CClHCH_3$ | 20.6 | 4.4 |
| FF | $CF_2HC(CF_2H)(H)CClHCFH_2$ | 23.7 | 3.8 |
| GG | $CF_2HC(CF_2H)(H)CClHCF_2H$ | 25.2 | 3.6 |
| HH | $CF_2HC(CFH_2)(F)CClHCF_2H$ | 28.4 | 3.2 |

EXAMPLES 1-14

Each solvent listed in Table II above is added to mineral oil in a weight ratio of 50:50 at 27° C. Each solvent is miscible in the mineral oil.

Having described the invention in detail and by reference to preferred embodiments thereof, it will be apparent that modifications and variations are possible without departing from the scope of the invention defined in the appended claims.

What is claimed is:

1. A method of dissolving contaminants or removing contaminants from the surface of a substrae which comprises the step of:
   (a) contacting said substrate surface with a hydrochlorofluorocarbon from the class of hydrochlorofluorocarbons having a tertiary strucutre, 5 carbon atoms, 1 chlorine atom, 6 to 8 fluorine atoms, and OH rate constants between about 8 and about 15 cm$^3$/molecule/sec×10$^{-14}$ wherein said hydrochlorofluorocarbons are $CF_3C(CF_3)(H)CFClCH_3$; $CF_2ClC(CF_3)(H)CF_2CH_3$; $CF_2HC(CH_3)(Cl)CF_2CF_3$; $CF_3C(CH_3(Cl)CFHCF_3$; $CF_2HC(CH_3)(F)CF_2CF_2Cl$; $CFClHC(CH_3)(F)CF_2CF_3$; $CF_2HC(CH_3)(F)CFClCF_3$; $CF_3C(CH_3)(F)(CFHCF_2Cl$; $CF_2ClC(CH_3)(F)CFHCF_3$; $CF_2ClC(CF_2H)(F)CF_2CH_3$; $CF_3C(CF_3)(Cl)CH_2CFH_2$; $CF_3C(CF_2Cl)(F)CH_2CF_2H$; $CF_3C(CF_3)(H)CHClCH_3$; and $CF_3C(CF_3)(F)CH_2CClH_2$ as solvent and
   (b) substantially dissolving or removing said contaminants from said substrate surface.

2. The method of claim 1, where said hydrochlorofluorocarbons are $CF_3C(CF_3)(H)CFClCH_3$; $CF_2ClC(CF_3)(H)CF_2CH_3$; $CF_2HC(CH_3)(Cl)CF_2CF_3$; $CF_3C(CH_3)(Cl)CFHCF_3$; $CF_3C(CF_3)(H)CClHCH_3$; and $CF_3C(CF_3)(F)CH_2CH_2Cl$.

3. The method of claim 1 wherein said hydrochlorofluorocarbon is $CH_3C(CF_3)(H)CFClCH_3$.

4. The method of claim 1 wherein said hydrochlorofluorocarbon is $CF_2ClC(CF_3)(H)CF_2CH_3$.

5. The emthod of claim 1 wherein said hydrochlorofluorocarbon is $CF_2HC(CH_3)(Cl)CF_2CF_3$.

6. The method of claim 1 wherein said hydrochlorofluorocarbon is $CF_3C(CH_3)(Cl)CFHCF_3$.

7. The method of claim 1 wherein said hydrochlorofluorocarbon is $CF_2HC(CH_3)(F)CF_2CF_2Cl$.

8. The method of claim 1 wherein said hydrochlorofluorocarbon is $CFClHC(CH_3)(F)CF_2CF_3$.

9. The method of claim 1 wherein said hydrochlorofluorocarbon is $CF_2HC(CH_3)(F)CFClCF_3$.

10. The method of claim 1 wherein said hydrochlorofluorocarbon is $CF_3C(CH_3)(F)CFHCF_2Cl$.

11. The method of claim 1 wherein said hydrochlorofluorocarbon is $CF_2ClC(CF_3)(F)CFHCF_3$.

12. The method of claim 1 wherein said hydrochlorofluorocarbon is $CF_2ClC(CF_2H)(F)CF_2CH_3$.

13. The method of claim 1 wherein said hydrochlorofluorocarbon is $CF_3C(CF_3)(Cl)CH_2CFH_2$.

14. The method of claim 1 wherein said hydrochlorofluorocarbon is $CF_3C(CF_2Cl)(F)CH_2CF_2H$.

15. The method of claim 1 wherein said hydrochlorofluorocarbon is $CF_3C(CF_3)(H)CHClCH_3$.

16. The method of claim 1 wherein said hydrochlorofluorocarbon is $CF_3C(CF_3)(F)CH_2CClH_2$.

* * * * *